United States Patent
Fettkoetter et al.

(10) Patent No.: US 6,245,328 B1
(45) Date of Patent: Jun. 12, 2001

(54) **MIXTURES AND COMPOSITIONS SUITABLE FOR CONTROLLING *HYLOTRUPES BAJULUS* AND *PYRRHIDIUM SANGUINEUM***

(75) Inventors: Regine Fettkoetter; Konrad Dettner, both of Bayreuth; Uwe Noldt, Geesthacht; Frank Schröder, Hamburg; Franke Wittko, Reinbek, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/817,705

(22) PCT Filed: Oct. 28, 1995

(86) PCT No.: PCT/EP95/04236

§ 371 Date: May 5, 1997

§ 102(e) Date: May 5, 1997

(87) PCT Pub. No.: WO96/13976

PCT Pub. Date: May 17, 1996

(30) Foreign Application Priority Data

Nov. 3, 1994 (DE) ................................................ 44 39 223

(51) Int. Cl.[7] .......................... A01N 35/02; A01N 35/00; A01N 31/02

(52) U.S. Cl. ............................. 424/84; 514/675; 514/724

(58) Field of Search .............................. 424/84; 514/675, 514/724

(56) References Cited

PUBLICATIONS

Chemical Abstracts 32 (13): 7016e, Jul. 1938.*
Fettkoether, R. et al., The male pheromone of the old house borer *Hylotrupes bajulus* (L.) (coleoptera:Cerambycidae): identification and female response, Experientia, 51(3), 270–277, Mar. 1995.*
Schroder, F. et al., Synthesis of (3R)–hydroxy–2–hexanone, (2R,3R)–2,3–hexanediol and (2S,3R)–2,3–hexanediol, the male sex pheromone of *Hylotrupes bajulus* and *Pyrrhidium sanguineum* (Cerambycidae), Liebigs Annalen der Chemie, vol. 1994, issue 12, 1211–1, Dec. 1994.*

* cited by examiner

Primary Examiner—John Pak
(74) Attorney, Agent, or Firm—Oblon, Spivak, McClelland, Maier & Neustadt, P.C.

(57) ABSTRACT

A mixture containing one stereoisomer of 3-hydroxyhexan-2-one and two stereoisomers of hexane-2,3-diol, especially (3R)-3-hydroxy-hexan-2-one, (2R,3R)-hexane-2,3-diol and/or (2R,3R)-hexane-2,3-diol and compositions containing them and the use of the mixture and of the compositions for controlling *Hylotrupes bajulus* and *Pyrrhidium sanguineum* by means of the monitoring, capture or mating disruption method are described.

20 Claims, 1 Drawing Sheet

MIXTURES AND COMPOSITIONS SUITABLE FOR CONTROLLING *HYLOTRUPES BAJULUS* AND *PYRRHIDIUM SANGUINEUM*

This application is a 371 of PCT/EP95/04236, filed on Oct. 28, 1995.

BACKGROUND OF THE INVENTION

1. Field of the Invention

The present invention relates to mixtures and compositions suitable for controlling *Hylotrupes bajulus* and *Pyrrhidium sanguineum* and their use for this purpose.

2. Description of the Background Art

In cases in which the control of insect pests using conventional insecticides is not indicated, for example in the treatment of structural timber in residential buildings, there is great interest in a biological pest control which can be selectively directed against a single type of pest or a small group of pests.

Methods of pest control in which the sex attractants or pheromones (attractants in the following) of the particular pests are used are generally known (cf. DE-A 36 03 377 [control of the vine moth] or WO-A 93/08148 [control of the cobbling moth]).

Especially *Hylotrupes bajulus* and in addition *Pyrrhidium sanguineum* are important wood pests, because their larvae bore into wood and destroy it.

*Hylotrupes bajulus* and *Pyrrhidium sanguineum* belong to the Cerambycidae family (round-headed borers), in which the involvement of attractants in mating behavior has already been studied for a long time. Contact pheromones or pheromones which act at short distances (short-range pheromones) have already been found in females of various round-headed borer species (cf. USDA Forest Service Research Note NE-240, 1 (1977); Appl. Ent. Zool. 27 (1992), page 489; J. Chem. Ecol. 18 (1992), page 245; ibid., 19 (1993), page 2347). In the case of *Hylotrupes bajulus*, it was suspected that the females form an attractant on their elytra which is used for finding a mate.

There is a study on an attractant which is released by the males (cf. Chem. Lett. (1984), page 263; Appl. Ent. Zool. 17 (1982), page 497; ibid. 21 (1986), page 606).

As a rule, from economic points of view it makes little sense for pest control to isolate the natural attractants from the pests producing them, because they are only there in low concentration. Instead of this, the search is aimed mostly at synthetically produced natural substances, or synthetic substances structurally related to these.

OBJECTS OF THE INVENTION

It is an object of the present invention to control *Hylotrupes bajulus* and *Pyrrhidium sanguineum* by means of synthetic attractants which are either natural, or related in terms of chemical structure to the natural attractants.

SUMMARY OF THE INVENTION

We have found that this object is achieved by a mixture which contains one stereoisomer of 3-hydroxyhexan-2-one and two stereoisomers of hexane-2,3-diol.

Mixtures were also found in which the abovementioned stereoisomers have specific configurations of the asymmetric carbon atoms and are furthermore present together in specific quantitative ratios.

In addition, the invention relates to compositions based on the abovementioned mixtures and additionally the use of the mixtures, compositions and of (3R)-3-hydroxyhexan-2-one for controlling *Hylotrupes bajulus* and *Pyrrhidium sanguineum*.

DETAILED DESCRIPTION OF THE INVENTION

Figure 1:
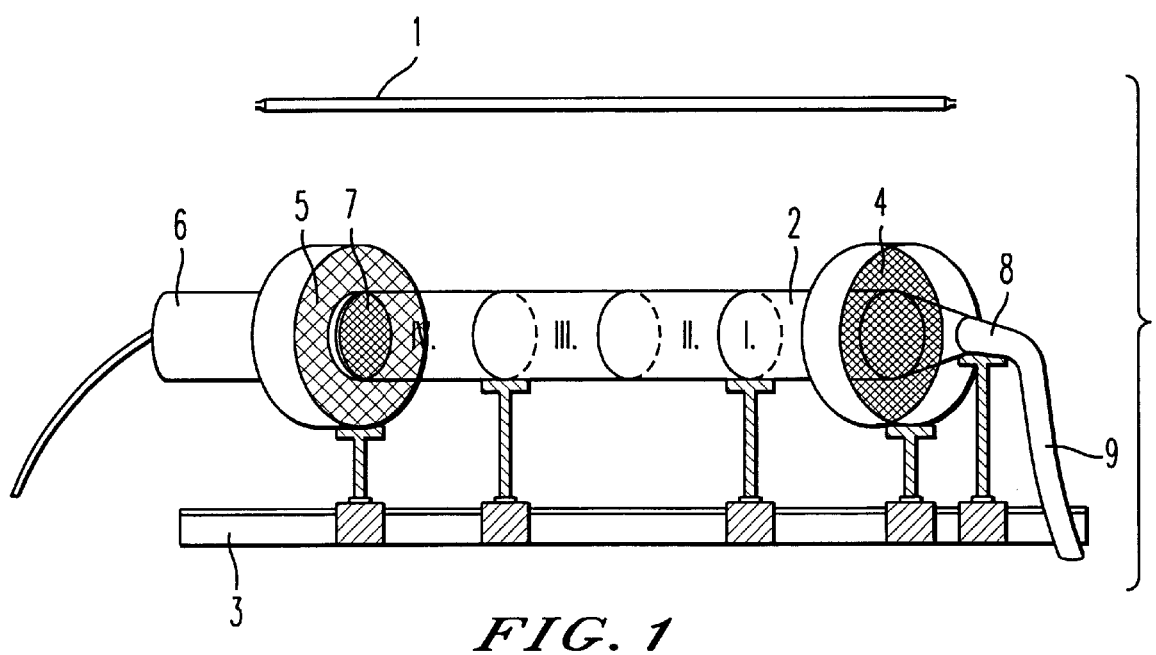
FIG. 1: schematic diagram of the wind tunnel described in Example 8 below.

There are fundamentally three different possibilities for using attractants in crop and material protection:

1. Monitoring Technique

Pheromone traps, equipped with synthetic attractant lures, are suspended in potential infestation areas. The capture of female beetles using traps furnishes proof of the occurrence of the pest. Additionally, information on the intensity of the attack and on the correct time for control can be derived.

2. Capture Technique

The attractant can be combined with insecticidal active compounds. There is the possibility of adding insecticides to the lure or to the trap or else of treating only in the immediate vicinity of the trap in order that the largest part of the female beetle population attracted from a wide range can then be killed. The biotope loading is reduced to a justifiable extent.

3. Mating Disruption Method

Finally, the pest can be controlled by the method of atmospheric saturation with attractants or similarly acting substances. The female beetles are disrupted from finding the males. As a result, mating of the animals is prevented. In this case, a greater amount of the attractant is dispersed in the atmosphere in the entire area of the plant crop to be protected such that the females can sense the presence of the scent everywhere and thus their normal orientation behavior is disrupted.

Above all, the third method (mating disruption method) is an extremely selective and also effective possibility for controlling an undesirable species while sparing the non-target organisms, in particular all useful insects.

According to this method, too only comparatively small amounts of the active compounds, which often correspond to only fractions of the usual doses of the conventional insecticidal active compounds, are required (cf. Birch (ed.), Pheromones, North Holland Publ. Co., 1974).

Methods 1 and 2 are disadvantageous inasmuch as the attractant of synthetic origin must be exactly equal to its natural prototype with respect to structure and purity (Minks and Voermann, Entomologia exp. and appl. 16 (1973), pages 341 to 349 and Wegler, Chemie der Pflanzenschutz- und Schädlingsbekamp-fungsmittel [Chemistry of crop protection agents and pesticides] vol. 6 (1981), p. 167). Technical mixtures or the like have regularly failed in capture experiments using traps.

All three techniques can be used in controlling, according to the invention, *Hylotrupes bajulus* and *Pyrrhidium sanguineum*.

It was found that the males of *Hylotrupes bajulus* and *Pyrrhidium sanguineum* produce attractants for their females, which essentially contain (3R)-3-hydroxyhexan-2-one, (2S,3R)-hexane-2,3-diol and (2R,3R)-hexane-2,3-diol and possibly hexane- 2,3-dione and/or racemic 2-hydroxyhexan-3-one (cf. R. Fettköther, K. Dettner, F. Schröder, H. Meyer, W. Francke and U. Noldt in Experientia, 1994, in print; F. Schröder, U. Noldt, R. Fettköther, K. Dettner, W. A. König and W. Francke in Liebigs Ann. Chem., 1994, in print).

It was furthermore found that for the method of mating disruption in *Hylotrupes bajulus* or *Pyrrhidium sanguineum* mixtures are suitable which contain any desired stereoisomer of 3-hydroxyhexan-2-one and any two desired stereoisomers of hexane-2,3-diol or in which these stereoisomers are only partly present in the naturally occurring stereospecific form.

It is preferred in the control of said round-headed borers by means of the mating disruption method, and essential in the capture technique or the monitoring technique, that (3R)-3-hydroxyhexan-2-one is used as the 3-hydroxyhexan-2-one and/or (2S,3R)-hexane-2,3-diol and (2R,3R)-hexane-2,3-diol are used as stereoisomers of hexane-2,3-diol.

Against both beetle pests, a mixture has proven effective which contains
a) from 70 to 100 parts by weight of (3R)-3-hydroxyhexan-2-one,
b) from 0.01 to 7, especially 3 parts by weight of (2R,3R)-hexane-2,3-diol,
c) from 0.01 to 20, especially 10 parts by weight of (2S,3R)-hexane-2,3-diol and if desired
d) from 0.01 to 5 parts by weight of hexane-2,3-dione and/or
e) from 0.01 to 7 parts by weight of a racemic mixture of 2-hydroxyhexan-3-one.

Advantageously, the (3R)-3-hydroxyhexan-2-one in this case has an excess ("ee value") of from 70 to 100, in particular from 90 to 100%, relative to its enantiomers.

It is furthermore advantageous if the (2S,3R)-hexane-2,3-diol has an excess of from 20 to 50, especially from 30 to 40%, relative to its enantiomers and the (2R,3R)-hexane-2,3-diol has an excess of from 15 to 45, in particular from 25 to 35%, especially in the case of *Hylotrupes bajulus* a ratio of (2S,3R)-hexane-2,3-diol to the diastereomeric (2E,3R)-hexane-2,3-diol of from 3:1 to 4:1 furthermore being preferred.

It has also been found that (3R)-3-hydroxyhexan-2-one is active per se in the mating disruption technique, the capture technique and the monitoring technique. It is also a part of the invention that even mixtures on their own of any two desired stereoisomers of hexane-2,3-diol are suitable for the mating disruption method and mixtures of (2S,3R)-hexane-2,3-diol and (2R,3R)-hexane-2,3-diol are suitable for the capture method or the monitoring method.

As far as the mixtures of (2S,3R)-hexane-2,3-diol and (2R,3R)-hexane-2,3-diol are concerned here, weight ratios of from 10 to 1 to from 1 to 1 are preferred and of from 5 to 1 to from 2 to 1 are particularly preferred. Furthermore, in them the (2S,3R) isomer preferably has an ee value of from 20 to 60, and the (2R,3R) isomer one of from 20 to 60.

In the case of *Hylotrupes bajulus*, a mixture has proven particularly effective as an attractant which contains
a) from 70 to 80 parts by weight of (3R)-3-hydroxyhexan-2-one, especially having an ee value of from 95 to 100%,
b) from 4 to 7 parts by weight of (2R,3R)-hexane-2,3-diol, especially having an ee value of from 30 to 40%,
c) from 14 to 19 parts by weight of (2S,3R)-hexane-2,3-diol, especially having an ee value of 25 to 35% and
d) from 1 to 4 parts by weight of hexane-2,3-dione and
e) from 0.5 to 4 parts by weight of a racemic mixture of 2-hydroxyhexan-3-one.

It has been established here that the presence of the components (d) and (e) is not essential for the action of this mixture, which is suitable as an attractant, against the females of *Hylotrupes bajulus*.

Furthermore, in the case of *Pyrrhidium sanguineum* a particularly effective mixture of the following composition was found:
a) from 92 to 100 parts by weight of (3R)-3-hydroxyhexan-2-one, especially having an ee value of from 95 to 100%,
b) from 0.01 to 1 part by weight of (2R,3R)-hexane-2,3-diol, especially having an ee value of from 85 to 95%,
c) from 0.01 to 1 part by weight of (2S,3R)-hexane-2,3-diol, especially as a racemate and
d) from 0.5 to 7 parts by weight of a racemic mixture of 2-hydroxyhexan-3-one.

The presence of the component (d) is not essential for the action of this mixture against the females of *Pyrrhidium sanguineum*. The abovementioned particularly effective mixtures are especially suitable for the monitoring technique and the capture technique.

The mixtures suitable as attractants are obtainable by organic chemical synthesis by preparing the components, ie. the individual substances or, in particular in the case of racemates, substance mixtures of the (stereo)chemical purity necessary in each case and then mixing them with one another in the appropriate ratio.

The operation is preferably carried out by stereoselectively preparing (3R)-3-hydroxyhexan-2-one, (2S,3R)-hexane-2,3-diol and (2R,3R)-hexane-2,3-diol having ee values or de values of >95% and mixing with racemic mixtures of 3-hydroxyhexan-2-one and/or hexane-2,3-diol in a ratio whose calculation is routinely performed by the person skilled in the art, and if desired adding the prespecified amount of hexane-2,3-dione and/or racemic 2-hydroxyhexan-3-one.

The synthesis of these individual substances and racemates is carried out according to the following schemes.

(3R)-3-Hydroxyhexan-2-one:

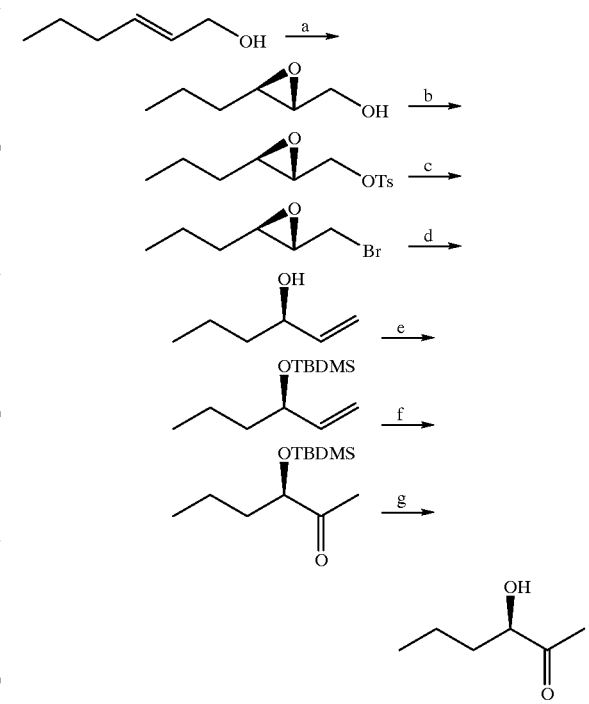

Ts=toluene-4-sulfonyl radical; TBDMS=tert-butyldimethylsilyl radical
a: tert-butyl hydroperoxide, diisopropyl D-(−)-tartrate, titanium(IV) isopropoxide
b: p-toluenesulfonyl chloride, potassium hydroxide c: lithium bromide
d: zinc, sodium iodide
e: tert-butyldimethylsilyl chloride, imidazole
f: palladium(II) chloride, copper(I) chloride, O$_2$
g: hydrofluoric acid (2S,3R)-Hexane-2,3-diol:

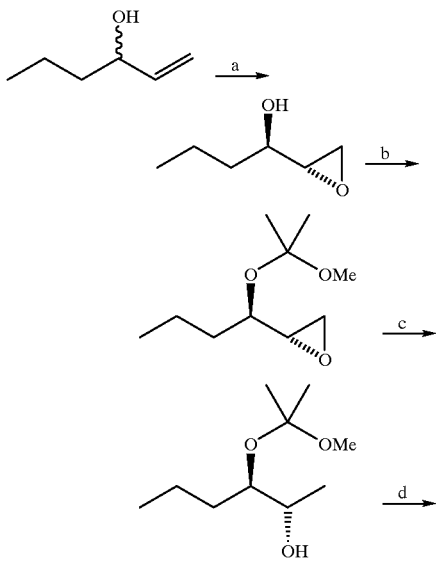

a: tert-butyl hydroperoxide, diisopropyl D-(−)-tartrate, titanium(IV) isopropoxide
b: p-toluenesulfonyl chloride, potassium carbonate, 2-methoxypropene
c: lithium aluminum hydride
d: hydrochloric acid (2R,3R)-Hexane-2, 3-diol;

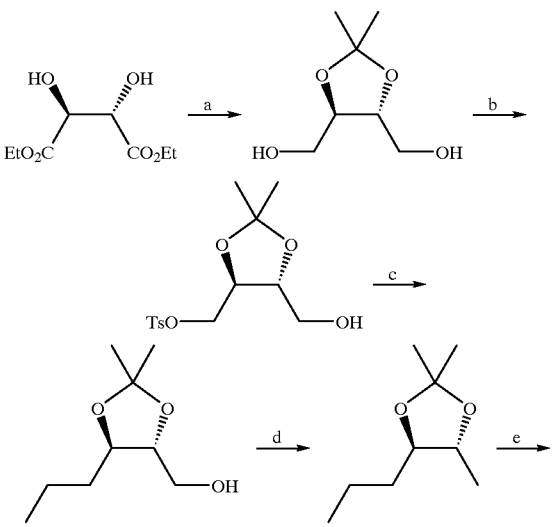

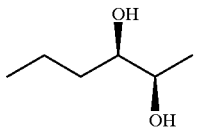

a: cf. J. Org. Chem. 33 (1968), page 2171
b: n-butyllithium, p-toluenesulfonyl chloride
c: ethylmagnesium bromide, copper(I) bromide/dimethyl sulfide
d: p-toluenesulfonyl chloride, potassium hydroxide; lithium. aluminum hydride
e: hydrochloric acid Racemates of 3-hydroxyhexan-2-one, 2-hydroxyhexan-3-one and hexane-2,3-iol:

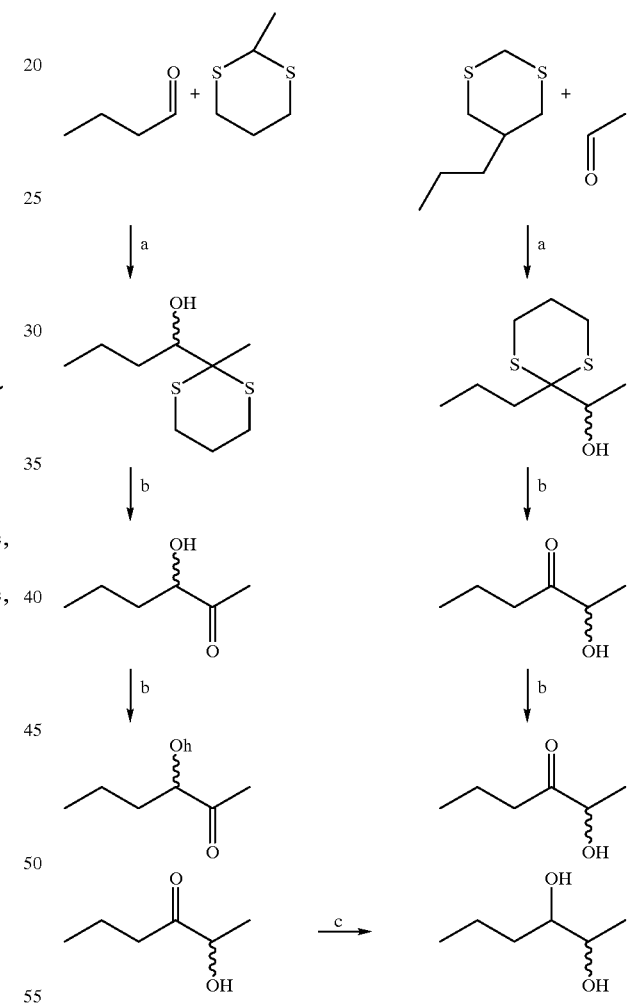

a: n-butyllithium
b: N-iodosuccinimide
c: lithium aluminum hydride

Hexane-2,3-dione is commercially available.

The reaction mixtures are worked up in a customary manner, eg. by mixing with water, separating the phases and if appropriate purifying the crude products by chromatography. The intermediates and final products are in some cases obtained in the form of colorless or slightly brownish, viscous oils which are freed from volatile components or purified under reduced pressure and at moderately elevated temperature. If the intermediates and final products are obtained as solids, the purification can also be carried out by recrystallizing or digesting.

For comparison purposes, natural attractants were also obtained from the males of *Hylotrupes bajulus* or *Pyrrhidium sanguineum*. This was carried out by means of closed loop stripping analysis (CLSA), in which the attractants are carried away from the insects in a closed apparatus by means of a gas stream, adsorbed on active carbon, and extracted from this by means of an organic solvent (cf. Analysis of Volatiles (ed.: Schreier, P.), Verlag de Gruyter, Berlin, 1984 and Journal of High Resolution Chromatography and Chromatography Communications 7 (1984), 492–494).

Suitable solvents here are hydrocarbons, halohydrocarbons, alcohols, ethers and esters or mixtures of these solvents. Solvents having boiling points below those of the attractant components are preferably used and in particular n-pentane, n-hexane, methanol or dichloromethane or mixtures thereof.

The mixtures according to the invention can be applied together with customary auxiliaries, eg. appropriately prepared strips of plastic, binding threads, attractant-filled ampoules or the like (for example according to the earlier German Application P 41 01 878.8) and can also contain preparation-related impurities.

Both liquid and solid preparations are suitable for formulation of the mixture. Suitable solvents are high-boiling, aromatic, aliphatic or cycloaliphatic compounds. Besides hydrocarbons, esters, ethers or ketones are particularly highly suitable. Typical representatives of these classes are eg. xylene, methylnaphthalenes, paraffin oils, cyclohexanone, ethylene glycol acetate, isophorone and dibutyl phthalate. These solvents can be used on their own or in mixtures with other components. Solutions in vegetable, animal or synthetic oils or fats and other evaporation-inhibiting solvents having a low vapor pressure such as eg. dioctyl phthalate can furthermore be prepared for the purposes of prolonging the action.

In addition, it is possible to bind the mixture in or on natural or synthetic solid carriers such as rubber, cork, cellulose, plastics, ground coal, wood meal, silicates, pumice grit, calcined clay or similar solid carriers or to employ it in special capsule formulations or plastic containers in order thus to achieve a uniform release into the air over relatively long periods. Additionally, the attractant can be evaporated from suitable containers, eg. capillaries or other vessels, through narrow openings or by diffusion through the container wall as well as from multilayer plastic platelets (flakes), whereby particularly uniform scent concentrations are achieved over relatively long periods.

The mixture content of these preparations can vary within wide limits. In capsule formulations or other suitable containers the ratio active compound:additive can be eg. in the range from 10:1 to 1:10³. In capsule formulations or other suitable containers the active compound can be used eg. in pure, undiluted form and its proportion by weight, based on the total formulation, can be very high and up to 90%. In general, however, very low active compound concentrations in the preparations are sufficient in order to exert the desired effect on the females of *Hylotrupes bajulus* and/or *Pyrrhidium sanguineum*. A quantitative ratio of active compound:additive of from 1:3 to 1:10², in particular from 1:10 to 1:100, is preferred.

A particular advantage of the mixtures and compositions according to the invention is that their application as a rule makes the use of customary synthetic insecticides unnecessary. According to previous knowledge, however, the additional use of the latter does not conflict from a technical point of view.

EXAMPLES (Column Chromatography: Flash Chromatography on Silica Gel (Silica Gel 60, 240–400 Mesh from Merck, Darmstadt, Germany); Gas Chromatography: Fisons GC 8000, Split Injector, FID, Hydrogen as Carrier Gas)

Example 1

Preparation of (3R)-3-hydroxyhexan-2-one a) (2R,3R)-2,3-Epoxyhexan-1-ol

Powdered activated molecular sieve (4 Å, 6 g), 2.13 g (7.5 mmol) of titanium(IV) isopropoxide and 27 g (300 mmol) of tert-butyl hydroperoxide were added in succession to a solution of diisopropyl D-(−)-tartrate (2.11 g, 9 mmol) in dry dichloromethane (300 ml) at −20° C. under argon. The mixture was additionally stirred at −20° C. for 20 minutes. 15 g (150 mmol) of freshly distilled (E)-2-hexen-1-ol in 70 ml of dry dichloromethane were then added in the course of 30 minutes. The mixture was stirred at −20° C. for a further 3 hours. It was then slowly poured into an ice-cold solution of 45 g (0.3 mol) of tartaric acid and 50 g (0.18 mol) of iron(II) sulfate heptahydrate in 300 ml of water. The mixture resulting in this way was vigorously stirred for 20 minutes. The organic phase was separated off, and the aqueous phase was extracted twice with 100 ml of dichloromethane in each case. The combined organic phases were washed with water and concentrated sodium chloride solution and dried over anhydrous sodium sulfate, and the solvent was then removed. Chromatography on 900 g of silica gel (30–70% by volume of ethyl acetate in n-hexane) followed. The yield of (2R,3R)-2,3-epoxyhexan-1-ol after distillation was 88.7% (b.p.: 85° C./14 hPa; yellow oil; $[\alpha]_D^{21}$=+45.6° (c=2.0 in trichloromethane); literature: $[\alpha]_D^{25}$=−46.30 (c=3.87 in trichloromethane) for the enantiomer (cf. J. Am. Chem. Soc. 109 (1987), page 5765).

b) (2R,3R)-2,3-Epoxyhexyl p-toluenesulfonate 26 g of powdered potassium hydroxide (0.45 mol) and 14.3 g (75 mmol) of p-toluenesulfonyl chloride were added in succession at −10° C. to a stirred solution of (2R,3R)-2,3-epoxy-1-hexanol (8 g, 69 mmol) in diethyl ether. After 5 hours at 0° C., the reaction mixture was poured into 200 ml of water. The organic layer was separated off and the aqueous phase was extracted twice with 100 ml of diethyl ether in each case. The combined organic phases were washed with concentrated sodium chloride solution and dried over anhydrous sodium sulfate. After removing the solvent, (2-R,3R)-2,3-epoxyhexyl p-toluenesulfonate remained in the form of light yellow crystals which crystallized from diethyl ether/n-hexane as colorless needles (yield: 71%; $[\alpha]_D^{20}$=+36.3°(c=2.0 in trichloromethane)).

The optical purity was determined by means of chiral gas chromatography. In this, the enantiomers (2S,3S)-2,3-epoxyhexyl p-toluenesulfonate and (2R,3R)-2,3-epoxyhexyl p-toluenesulfonate were separated at 155° C. on a 20 m-long quartz glass column having an internal diameter of 0.25 mm, which was coated with heptakis[2,3-di-O-methyl-6-O-({1,1,2-trimethylpropyl}dimethyl-silyl)]-β-icyclodextrin. The (2S,3S) isomer had an $R_t$ value (retention time) of 32.82, its enantiomer of 34.12 minutes. After recrystallization, the ee value of the (2R,3R) isomer was about 99%.

c) (2S,3R)-1-Bromo-2,3-epoxyhexane

A solution of (2R,3R)-2,3-epoxyhexyl p-toluenesulfonate (13 g, 48.1 mmol) and lithium bromide (16 g, 0.186 mmol) in dry acetone (200 ml) was refluxed for 30 minutes. After removing the solvent, 200 ml of water and 100 ml of diethyl ether were added. The organic phase was separated off and the aqueous phase was extracted twice with 50 ml of diethyl ether in each case. The combined organic phases were washed with saturated sodium hydrogen carbonate solution and concentrated sodium chloride solution. After drying over anhydrous sodium sulfate, the solvent was removed. The residue was chromatographed on 400 g of silica gel (eluent: 20% by volume ethyl acetate in n-hexane). The yield was 96.4% (colorless oil; $[\alpha]_D^{19}$=+12.5° (c=2.8 in trichloromethane)).

d) (3R)-1-Hexen-3-ol

A mixture of (2S,3R)-1-bromo-2,3-epoxyhexane (5.42 g, 30.2 mmol), sodium iodide (12 g, 80 mmol) and zinc dust (5.9 g, 90 mmol) in 60 ml of dry methanol was refluxed under argon for 4 hours and, after cooling, poured into a mixture of 100 ml of diethyl ether, 100 ml of n-pentane and 200 ml of water. After filtration, the organic phase was separated off, and the aqueous phase was extracted twice with 50 ml of diethyl ether in each case. The combined organic phases were washed with concentrated sodium chloride solution. The residue obtained after drying over anhydrous sodium sulfate and concentrating at 400/200 hPa was distilled. (3R)-1-Hexen-3-ol was obtained as a colorless oil in 74.7% yield (b.p.: 70–72° C./120 hPa; $[\alpha]_D^{20}$==14.7 (c=1.9 in trichloromethane)).

The optical purity was determined by means of chiral gas chromatography. In this, the enantiomers (3R)-1-hexen-3-ol and (3S)-1-hexen-3-ol were separated at 45° on a 24 m-long quartz glass column of internal diameter 0.25 mm, which was coated with octakis(6-O-methyl-2,3-di-pentyl)-γ-cyclodextrin. The (3R) isomer had an $R_t$ value of 19.8, its enantiomer of 21.2 minutes. The ee value of the (3R) isomer was about 99%.

e) (3R)-3-(tert-Butyldimethylsilyloxy)-1-hexene 3.8 g (24 mmol) of tert-butyldimethylsilyl chloride were added at –10° C. over the course of 10 minutes in 5 portions to a stirred solution of 2.05 g (20.5 mmol) of (3R)-1-hexen-3-ol and 3.4 g (49 mmol) of imidazole in 50 ml of dry dimethylformamide. After 3 hours at 0° C., the reaction mixture was poured into 200 ml of saturated aqueous sodium hydrogen carbonate solution. The mixture was extracted three. times with 50 ml of n-hexane in each case. The combined organic phases were washed with water and concentrated sodium chloride solution. After drying over anhydrous sodium sulfate and removing the solvent, the residue was chromatographed on 300 g of silica gel. The eluent used was a mixture of 5% by volume ethyl acetate in n-hexane. (3R)-3-(tert-butyldimethylsilyloxy)-1-hexene was obtained as a colorless oil in 91.6% yield ($[\alpha]_D^{19}$=–5.3° (c=2.4 in trichloromethane)).

f) (3R)-3-(tert-Butyldimethylsilyloxy)-hexan-2-one

A mixture of 0.39 g of palladium(II) chloride (0.22 mmol) and 2.2 g of copper(I) chloride (22 mmol) in 10 ml of water and 70 ml of absolute dimethylformamide was vigorously stirred at 60° C. in an oxygen atmosphere for 1 hour. 3.63 g (16.9 mmol) of (3R)-3-(tert-butyldimethylsilyloxy)-1-hexene were then added. The mixture thus obtained was stirred at 60° C. for 30 minutes. After addition of 300 ml of water and 100 ml of n-hexane, the organic phase was separated off and the aqueous phase was extracted twice with 50 ml of n-hexane in each case. The combined organic phases were washed in succession with a saturated aqueous sodium hydrogen carbonate solution and concentrated sodium chloride solution. After drying over anhydrous sodium sulfate, the organic phase was concentrated and the residue was chromatographed on 300 g of silica gel using 10% by volume tert-butyl methyl ether in n-hexane as an eluent.

(3R)-3-(tert-Butyldimethylsilyloxy)hexan-2-one was obtained in a yield of 65.1% as a colorless oil ($[\alpha]_D^{20}$=+33.70 (c=2.1 in trichloromethane)).

g) (3R)-3-Hydroxyhexan-2-one 1 ml of 40% strength by weight hydrofluoric acid was added to a solution of 2.3 g (10 mmol) of (3R)-3-(tert-butyldimethylsilyloxy)hexan-2-one in 15 ml of acetonitrile. After the reaction mixture had been stirred at 20° C. for 3 hours, it was poured into 100 ml of a saturated aqueous sodium hydrogen carbonate solution. The mixture was extracted three times with 50 ml of diethyl ether in each case. The combined diethyl ether extracts were washed with concentrated sodium chloride solution and dried over anhydrous sodium sulfate. After concentrating the solvent, a yellow oil remained which was chromatographed on 100 g of silica gel using 20–40% by volume of diethyl ether in n-pentane as the eluent. (3R)-3-Hydroxyhexan-2-one was obtained as a colorless oil in a yield of 90% ($[\alpha]_D^{20}$=–1100 (c=0.8 in trichloromethane)).

The optical purity was determined by means of chiral gas chromatography. In this, the enantiomers (3R)-3-hydroxy-hexan-2-one and (3S)-3-hydroxyhexan-2-one were separated at 70° C. on a 25 m-long quartz glass column of internal diameter 0.25 mm, which was coated with heptakis (2,6-dimethyl-3-pentyl)-β-cyclodextrin. The (3R) isomer had an $R_t$ value of 4.16, its enantiomer of 6.02 minutes. The ee value of the (3R) isomer was about 99%.

Example 2

Preparation of (2S,3R)-hexane-2,3-diol a) (2S,3R)-1,2-Epoxy-3-hexanol

Powdered activated molecular sieve (4 Å, 10 g), 4.55 g (16 mmol) of titanium(IV) isopropoxide and 18.1 g (200 mmol) of tert-butyl hydroperoxide were added in succession to a solution of diisopropyl D-(–)-tartrate (4.48 g, 20 mmol) in dry dichloromethane (200 ml) at –30° C. under argon. The mixture was additionally stirred at –30° C. for 20 minutes. 9 g (90 mmol) of freshly distilled 1-hexen-3-ol in 50 ml of dry dichloromethane were then added in the course of 15 minutes. The mixture was additionally stirred at –30° C. for 48 hours. It was then slowly poured into an ice-cold solution of 30 g (0.2 mol) of tartaric acid and 33 g (0.12 mol) of iron(II) sulfate heptahydrate in 200 ml of water. The mixture thus formed was vigorously stirred for 20 minutes. The organic phase was separated off, and the aqueous phase was extracted twice with 50 ml of dichloromethane in each case. The combined organic phases were washed with water and concentrated sodium chloride solution and dried over anhydrous sodium sulfate, and the solvent was then removed.

Chromatography of the residue on 700 g of silica gel (25–50% by volume of ethyl acetate in n-hexane) followed. The yield of (2S,3R)-1,2-epoxy-3-hexanol was 79% (colorless oil; $[\alpha]_D^{20}$=–24.3° (c=1.8 in trichloromethane)).

The optical purity was determined by means of chiral gas chromatography. In this, the enantiomers (2B,3R)-1,2-epoxy-3-hexanol and (2R,3S)-1,2-epoxy-3-hexanol were separated using a temperature program (3 minutes 60° C., then at 5° C./min to 120° C.) on a 25 m-long quartz glass column of internal diameter 0.25 mm, which was coated with heptakis(2,6-di-O-methyl-3-O-pentyl)-β-cyclodextrin. The (2R,3S) isomer had an $R_t$ value of 7.95, its enantiomer of 8.22 minutes. The ee value of the (2S,3R) isomer was about 97%.

b) (2S,3R)-1,2-Epoxy-3-(2-methoxy-2-methylethoxy) hexane 10 mg of p-toluenesulfonic acid were added at 0° C. to 2.9 g (25 mmol) of (2S,3R)-1,2-epoxy-3-hexanol in 8 g (0.11 mmol) of 2-methoxypropene. After stirring at 20° C. for 30 minutes, 30 mg of potassium carbonate were added. The mixture was concentrated under reduced pressure, and the residue was then chromatographed on 300 g of silica gel. The eluent used was n-pentane containing 20–30% by volume of diethyl ether and 0.2% by volume of triethylamine. The yield of (2S,3R)-1,2-epoxy-3-(2-methoxy-2-methylethoxy)hexane, a colorless oil, was 83% ($[\alpha]_D^{20}$=−32.50 (c=2.0 in dichloromethane)).

c) (2S,3R)-3-(2-Methoxy-2-methylethoxy)hexan-2-ol 3.62 g (19.2 mmol) of (2S,3R)-1,2-epoxy-3-(2-methoxy-2-methylethoxy)hexane in 30 ml of diethyl ether were added dropwise at 0° C. under argon over the course of 15 minutes to a stirred suspension of 0.85 g (22.2 mmol) of lithium aluminum hydride in 100 ml of diethyl ether. The mixture was subsequently then stirred at 20° C. for 36 hours. The excess of lithium aluminum hydride was decomposed by cautious addition of 1.2 ml of water. After 5 minutes, 4 ml of a 10% strength by weight sodium hydroxide solution were added and the mixture was vigorously stirred for 10 minutes. The precipitate was then filtered off, and the filter residue was extracted three times with 50 ml of tetrahydrofuran. The combined organic phases were dried over anhydrous sodium sulfate and concentrated. The residue was distilled over potassium carbonate and yielded (2S,3R)-3-(2-methoxy-2-methylethoxy)hexan-2-ol in a yield of 83% (b.p.: 71–73° C./3 hPa; $[\alpha]_D^{19}$=−10.3° (c=2.3 in dichloromethane)).

d) (2S,3R)-Hexane-2,3-diol 5 ml of 1N hydrochloric acid were added to a solution of 2.7 g (14.2 mmol) of (2S,3R)-3-(2-methoxy-2-methylethoxy)hexan-2-ol in 10 ml of methanol. The mixture was stirred at 20° C. for 30 minutes and then poured into a solution of 5 g of potassium carbonate in 10 ml of water. 50 ml of concentrated sodium chloride solution were added and the mixture was extracted three times with 50 ml of ethyl acetate in each case. The combined organic phases were dried over anhydrous sodium sulfate and then concentrated. The residue was chromatographed on 100 g of silica gel using 40–70% by volume ethyl acetate in n-hexane as an eluent. (2S,3R)-hexane-2,3-diol was obtained after distillation as a colorless oil in a yield of 86.4% (b.p.: 103° C./19 hPa; crystallization after 30 minutes at 20° C.; $[\alpha]_D^{20}$=20.9° (c=1.4 in trichloromethane)).

The optical purity was determined by means of chiral gas chromatography. In this, the 4 stereoisomers were separated at 85° C. on a 25 m-long quartz glass column of internal diameter 0.25 mm, which was coated with heptakis(2,6-di methyl-3-pentyl)-3-cyclodextrin. $R_t$ values: (2S,3S) isomer 12.3, (2R,3R) isomer 14, (2R,3S) isomer 15.4 and (2S,3R) isomer 16.9 minutes. The ee value and the de value of the (2S,3R) isomer were about 96%.

Example 3

Preparation of (2R,3R)-hexane-2,3-diol a) (4R,5R)-[5-Hydroxymethyl-2,2-dimethyl-1,3-dioxolan-4-yl]-methyl P-toluenesulfonate 21.7 mmol of n-butyllithium (1.59 molar in n-hexane, 13.6 ml) were added at -78 C to a solution of (4R,5R)-4,5-bis(hydroxymethyl)-2,2-dimethyl-1,3-dioxolane (3.32 g, 20.5 mmol) in 60 ml of tetrahydrofuran ((4R,5R)-4,5-bis(hydroxymethyl)-2,2-dimethyl-1,3-dioxolane was prepared according to J. Org. Chem. 33 (1968), page 2171). After stirring for 10 minutes, a solution of p-toluenesulfonyl chloride (4 g, 21 mmol) in 20 ml of tetrahydrofuran which was cooled to −78° C. was added. After stirring at −78° C. for 15 minutes, the mixture was warmed to 20° C. and poured into 200 ml of concentrated sodium chloride solution. The organic phase was separated off and the aqueous phase was extracted twice with 50 ml of ethyl acetate. The combined organic phases were dried over anhydrous sodium sulfate and then concentrated. The residue was chromatographed on 400 g of silica gel using ethyl acetate and n-hexane in the weight ratio 60:40 as eluent. 74.6% of (4R,5R)-[5-hydroxymethyl-2,2-dimethyl-1,3-dioxolan-4-yl]methyl p-toluenesulfonate were obtained ($[\alpha]_D^{19}$=+11.80 (c=1.88 in trichloromethane); cf. J. Org. Chem. 55 (1990), page 4417: $[\alpha]_D^{21}$=+11.30 (c=2.70 in trichloromethane)).

b) (4R,5R)-(2,2-Dimethyl-5-propyl-1,3-dioxolan-4-yl) methanol 3.29 g (16 mmol) of copper(I) bromide/dimethyl sulfide and a Grignard reagent, prepared from 3.92 g (36 mmol) of ethyl bromide and 1.3 g (54 mmol) of magnesium in 60 ml of diethyl ether, were added in succession to a stirred solution of (4R,5R)-[5-hydroxymethyl-2,2-dimethyl-1,3-dioxolan-4-yl]methyl p-toluenesulfonate (4.62 g, 14.6 mmol) in 60 ml of tetrahydrofuran at -40° C. under argon. After stirring at 0° C. for 4 hours, the mixture was poured into a mixture of 200 ml of saturated aqueous ammonium chloride solution and 10 ml of saturated aqueous ammonia solution. The resulting 2-phase system was stirred for 20 minutes. The organic phase was then separated off and the aqueous phase was extracted with ethyl acetate. The combined organic phases were washed with saturated aqueous ammonium chloride, sodium hydrogen carbonate and concentrated sodium chloride solution. After drying over anhydrous sodium sulfate and removing the solvent, a residue remained which was chromatographed on 100 g of silica gel using ethyl acetate and n-hexane in the weight ratio 1:3 as eluent. (4R, 5R)-(2,2-Dimethyl-5-propyl-1,3-dioxolan-4-yl) methanol was obtained as a colorless oil in a yield of 83.3% ($[\alpha]_D^{20}$=+27.3° (c=2.81° in trichloromethane); cf. Liebigs Ann. Chem. (1975) page 2261: $[\alpha]_D^{25}$=−27.7° (c=2.8 in trichloromethane) for the enantiomer).

c) (4R,5R)-(2,2-Dimethyl-5-propyl-1,3-dioxolan-4-yl) methanol p-toluenesulfonate 2.29 g (12 mmol) of p-toluenesulfonyl chloride were added at 0° C. to a stirred mixture of 4.6 g (80 mmol) of powdered potassium hydroxide and 1.94 g (11.1 mmol) of (4R,5R)-(2,2-dimethyl-5-propyl-1,3-dioxolan-4-yl) methanol in 100 ml of diethyl ether. After stirring at 0° C. for 5 hours, the mixture was poured into 100 ml of water. The organic layer was separated off and the aqueous phase was extracted twice with 50 ml of diethyl ether. The combined organic phases were washed with a saturated aqueous sodium hydrogen carbonate and concentrated sodium chloride solution, dried over anhydrous sodium sulfate and then concentrated. The residue was chromatographed on 300 g of silica gel using n-hexane to which 15–30% by volume of ethyl acetate were admixed.

(4R,5R)-(2,2-Dimethyl-5-propyl-1,3-dioxolan-4-yl) methanol p-toluenesulfonate was obtained as a colorless oil in a yield of 91% ($[\alpha]_D^{20}$=21.20 (c=1.7 in trichloromethane)).

d) (4R,5R)-2,2,5-Trimethyl-4-propyl-1,3-dioxolane

A solution of (4R,5R)-(2,2-dimethyl-5-propyl-1,3-dioxolan-4- yl)methanol p-toluenesulfonate (3.04 g, 9.25 mmol) in 30 ml of diethyl ether was added dropwise at 0° C. and under argon to a stirred suspension of lithium aluminum hydride (0.380 g, 10 mmol) in 50 ml of diethyl ether. The mixture was additionally stirred at 20° C. for 24 hours. The excess of lithium aluminum hydride was destroyed by addition of 0.2 ml of water. After stirring for 5 minutes, the mixture was treated with 1.8 ml of 10% strength by weight sodium hydroxide solution. The resulting mixture was additionally stirred vigorously for a further 10 minutes. The precipitate was then filtered off and the filter residue was extracted three times with 50 ml of tetrahydrofuran in each case. The combined organic phases were dried over anhydrous sodium sulfate. After chromatography on 100 g of silica gel using n-pentane containing 10–20% by volume of diethyl ether as eluent, the residue yielded 92% of (4R,5R)-2,2,5-trimethyl-4-propyl-1,3-dioxolane as a colorless oil ($[\alpha]_D^{20}$=+6.28° (c=2.5 in trichloromethane)).

e) (2R,3R)-Hexane-2,3-diol 3 ml of 6 N hydrochloric acid were added to a solution of 1.13 g (7.14 mmol) of (4R,5R)-2,2,5-trimethyl-4-propyl-1,3-dioxolane in 5 ml of methanol and 3 ml of tetrahydrofuran at 0° C. The mixture was stirred at 20° C. for 60 minutes and then poured into a solution of 5 g of potassium carbonate in 20 ml of water. 50 ml of concentrated sodium chloride solution were added and the resulting mixture was extracted three times with 50 ml of ethyl acetate in each case. The combined organic phases were dried over anhydrous sodium sulfate, and then they were concentrated. The residue was chromatographed on 60 g of silica gel using 40–70% by volume of ethyl acetate in n-hexane and yielded, after distillation, (2R,3R)-hexane-2,3-diol as a colorless oil in a yield of 81% (b.p.: 102° C./17 hPa; $[\alpha]_D^{20}$=22.3° (c=1.22 in trichloromethane)).

The optical purity was determined by means of chiral gas chromatography. In this, the 4 stereoisomers were separated at 85° C. on a 25 m-long quartz glass column of internal diameter 0.25 mm, which was coated with heptakis(2,6-di-O-ethyl-3-O-pentyl)-β-cyclodextrin. $R_t$ values: (2S,3S) isomer 12.3, (2R,3R) isomer 14, (2R,3S) isomer 15.4 and (2S,3R) isomer 16.9 minutes. The ee value and the de value of the (2S,3R) isomer were >99.5%.

Example 4

Preparation of Racemic 3-hydroxyhexan-2-one a) 2-(1-Hydroxybutyl)-2-methyl-1,3-dithian 56 mmol of n-butyllithium (35 ml of a 1.6 M solution in hexane) were added with stirring to a solution of 2-methyl-1,3-dithian (7 g, 52.1 mmol) in 100 ml of dry tetrahydrofuran at −30° C. under argon. After stirring at −30° C. for 2 hours, the mixture was cooled to −78° C. 4.2 g (58.3 mmol) of freshly distilled n-butyraldehyde were added dropwise in the course of 15 minutes and the mixture was stirred for a further 30 minutes. After warming to 20° C., it was poured into a beaker containing 300 ml of water and 100 ml of n-hexane. The organic phase was separated off and the aqueous phase was extracted three times with 50 ml of dichloromethane in each case. The combined organic phases were washed with 10% strength by weight potassium hydroxide solution, water and concentrated sodium chloride solution, dried over anhydrous sodium sulfate and then distilled. 8.82 g of 2-(1-hydroxybutyl)-2-methyl-1,3-dithian were isolated as a colorless oil.

b) 3-Hydroxyhexan-2-one 6 g (29.1 mmol) of 2-(1-hydroxybutyl)-2-methyl-1,3-dithian were initially introduced into 70 ml of acetone and 10 ml of water. The mixture was cooled to -10° C. 13.5 g (60 mmol) of N-iodosuccinimide were added at this temperature and the whole was stirred at this temperature for a further hour. The mixture was then poured into 100 ml of saturated sodium thiosulfate solution, the whole was extracted three times with 50 ml of ethyl acetate in each case, and the combined organic phases were washed with saturated sodium thiosulfate solution, water and concentrated sodium chloride solution, dried over anhydrous sodium sulfate and concentrated. Column chromatography on 300 g of silica gel using 15–40% by weight of ethyl acetate in n-hexane as eluent yielded 2.21 g of the title compound as a colorless oil.

Example 5

Preparation of Racemic 2-hydroxyhexan-3-one a) 2-(1-Hydroxyethyl)-2-n-propyl-1,3-dithian The synthesis was carried out in a similar manner to Example 4/(a), but using 8 g (49.3 mmol) of 2-n-propyl-1,3-dithian, 52 mmol of n-butyllithium (32.5 ml of a 1.6 M solution in n-hexane) and 2.5 g (56.8 mmol) of acetaldehyde. 8.84 g of 2-(1-hydroxyethyl)-2-n-propyl-1,3-dithian were obtained as a colorless oil.

b) 2-Hydroxyhexan-3-one 2-(1-Hydroxyethyl)-2-n-propyl-1,3-dithian was cleaved to 2-hydroxyhexan-3-one in a similar manner to Example 4/(b), but using 1.5 g (7.3 mmol) of 2-hydroxyhexan-3-one and 3.37 g (15 mmol) of N-iodosuccinimide. Column chromatography on 60 g of silica gel using 15–30% by weight of ethyl acetate in n-hexane as eluent afforded 0.48 g of the title compound as a colorless oil.

Example 6

Preparation of Racemic hexane-2,3-diol 1.2 g (10 mmol) of racemic 2-hydroxyhexan-3-one in 30 ml of diethyl ether were added dropwise at 0° C. to a suspension of 750 mg (20 mmol) of lithium aluminum hydride in 50 ml of absolute diethyl ether. The mixture was subsequently stirred at 0° C. for 1 hour. 0.2 ml of water were then added. After addition of 2 ml of 10% strength by weight sodium hydroxide solution, the mixture was stirred for a further 10 minutes. The precipitate was filtered off and the filter cake was washed two more times with 30 ml of tetrahydrofuran in each case. The combined organic phases were dried over anhydrous sodium sulfate and then concentrated. After distillation under reduced pressure, 0.92 g of a mixture of (2S*,3R*)-hexane-2,3-diol and (2R*,3R*)-hexane-2,3-diol were obtained in the ratio 3:1 (b.p.: 100° C./17 hPa).

The notation eg. (2S*,3R*) means a ratio of (2.,3R) to (2R,3,) of 1:1, ie. a racemate of the pure diastereomers.

Example 7

Preparation of a Mixture According to the Invention 500 mg of a mixture of (2S*,3R*)-hexane-2,3-diol and (2R*,3R*)-hexane-2,3-diol in the ratio 77:23 and 230 mg of (2S,3R)-hexane-2,3-diol of ee value 96% and 55 mg of (2S,3R)-hexane-2,3-diol of ee value 99% were mixed at 80° C. for 30 minutes. 785 mg of a mixture of (2S,3R)-hexane-2,3-diol of 34% ee and (2R,3R)-hexane-2,3-diol of 32% ee were obtained in the ratio 78.5:21.5.

By addition of 200 mg of (3R)-3-hydroxyhexan-2-one (ee value: 99%, cf. Example 1) to 20 mg of the diol mixture according to Example 7, a mixture was obtained which had the composition below:

90.9 parts by weight of (3R)-3-hydroxyhexan-2-one (99% ee), 7.1 parts by weight of (23,3R)-hexane-2,3-diol (34% ee) and 2 parts by weight of (2R,3R)-hexane-2,3-diol (32% ee).

Example 8

Experiment in the Wind Tunnel with *Hylotrupes bajulus*

The test beetles came from a laboratory strain of *Hylotrupes bajulus*. Before experimental use, the beetles, after they appeared from their wooden breeding blocks, were kept individually for 8 days in plastic boxes containing moistened filter paper in order to be able to assume sexual maturity and readiness of the beetles for copulation. The beetles had to be supplied only with drinking water. Males and females were separated according to sex in 2 climatic chambers having a constant temperature of 20° C. and a 12:12 L:D photoperiod. The beetles which until use in the wind tunnel experiment had no contact with members of the same species were tested once in each of the experimental batches in the course of 7 days. During the experimental period, an age of 9–15 days resulted for the experimental animals which were ready for copulation. Females were observed in the act of copulation from the 3rd–19th day after appearance or hatching from their breeding wood.

After completion of the experimental batches in the wind tunnel using the virgin females, they were put together with a male in each case and separated again immediately after copulation. The copulated females were tested again in the wind tunnel 24 hours after copulation.

The experimental runs in the wind tunnel (see FIG. 1) were carried out in a climatic chamber at 30° C. and a relative atmospheric humidity of 20–30%. The experimental assembly was uniformly and constantly illuminated from above by means of fluorescent light from 8 neon tubes (1) above the wind tunnel (8000 lux measured in the wind tunnel tube). The wind tunnel consisted of an acrylic Plexiglass tube (2) of length 100 cm and internal diameter 19 cm which was subdivided into 4 zones (I.–IV.) of 25 cm in each case by markings. The wind tunnel tube was held by movable metal supports along a track (3). The two tube openings were closed on one side by a starting screen (4) and on the opposite side by a screen (5) directly in front of the fan (6). The experimental animals were put in at the starting screen, while the stimulants were simultaneously fastened to the fan screen in a gauze container (7=Petri dish with gauze cover and bottom; 14 cm diameter). The wind side of the fan was covered with several layers of gauze in order to obtain a uniform and laminar flow through the wind tunnel zones. The contaminated air which flowed out through the starting screen was led into the exhaust from the climatic chamber through a suction apparatus (9) by means of a glass funnel (8).

On average, the wind velocities in the tube were 0.65 m/sec at the starting screen, 0.71 m/sec in the center of the tube between zones II and III and 2.3 m/sec at the ventilator screen beside the gauze container. Directly before the gauze container, the wind velocity was reduced to 0.02 m/sec, as the wind had to pass through the two gauze layers of the dish cover and bottom.

The experimental runs were carried out between 12.00 and 17.00 in order to utilize the time frame of the daily activity of the beetles. In each test run, two experimental beetles were simultaneously put in at the starting screen and observed for an experimental period of 15 minutes. As stimulants, either living beetles or glass capillaries which were filled with hexane solutions of male CLSA filtrates or synthetic gland secretion components were enclosed in the gauze container. The experimental period and the capillary sizes had been selected such that toward the end of the experimental period of 15 minutes a complete evaporation of the hexane volume was guaranteed. Every 5 µl of hexane solution were presented in calibrated 5 µl micropipettes which were fixed horizontally in the gauze container for the experimental runs in the wind tunnel.

The following experimental batches were specifically tested:
1) control using an empty gauze container;
2) hexane control using 5 µl of n-hexane;
3) unmated females which were separated by cardboard strips in the gauze box and had no visual contact;
4) unmated males, likewise isolated by cardboard strips;
5) CLSA extract: a pheromone extract was obtained by means of closed loop stripping analysis (CLSA; cf. literature references in the description). 8 unmated males were put into a 110 ml glass container on a few filter paper strips. The paper strips served as isolation and a place for the beetles in the narrow container. For 24 hours under constant light conditions (from 8 neon tubes), the container air which was enriched with the attractants of the males was filtered using a 1.5 mg active carbon filter. The filter was extracted with 15 µl of n-hexane. The concentration of the pheromone in the hexane extract was checked by qualitatively analyzing 1 µl of hexane mixture in the GC/MS. The CLSA extract was only used in the wind tunnel experiment if the pheromone was detectable in the solvent. For 2 experimental runs, 5 µl of a CLSA extract were in each case put into the calibrated 5 µl capillaries (see above);
6) 5 µl of synthetic mixture: for supply of a synthetic attractant mixture in the wind tunnel, 50 mg of (3R)-3-hydroxyhexan-2-one (ee>99%), 15 mg of the diastereomeric diols (2R,3R)-hexane-2,3-diol (31% ee) and (2S,3R)-hexane-2,3-diol (34% ee) in the ratio 1:3 and 1.5 mg of hexane-2,3-dione (4) were dissolved in 5 ml of hexane. 5 µl of the synthetic mixture were supplied in each case;
7) 50 µl of synthetic mixture; the higher dose of the attractant supply was achieved by the complete evaporation of 50 µl of the synthetic solution (see stage 6) within 15 minutes by filling two 100 µl micropipettes with 25 µl of the pheromone solution in each case;
8) (3R)-3-hydroxyhexan-2-one: 50 µg of the synthetic main component (ee>99%) were contained in 5 µl of hexane;
9) (2R,3R)-hexane-2,3-diol and (2S,3R)-hexane-2,3-diol: 50 µg of the mixture of the diastereomeric diols were dissolved in the ratio 1 (31% ee): 3 (34% ee) in 5 µl of hexane;
10) hexane-2,3-dione: 50 µg were supplied in 5 Al of hexane.

The following behavior of the beetles was recorded:
Test beetles begin to run at the starting screen and reach zones I–IV; searching movement at the gauze container/restraint of the movements in the case of the odor source at the fan screen or the gauze container. The number of test beetles which reached the fixed marks or showed the defined behavior was statistically analyzed by the $\%^2$ test.

The results of the experiments can be seen from Table 1 which follows.

TABLE 1

Reaction of unmated females of Hylotrupes bajulus to various scent sources

| No. | Scent source | Number of unmated females (n) | Start (%) | Reaching | | | | Searching/staying in the vicinity of the scent source (%) |
| | | | | Zone I (%) | Zone II (%) | Zone III (%) | Zone IV (%) | |
|---|---|---|---|---|---|---|---|---|
| 1 | None (blank experiment) | 30 | 70 | 67 | 60 | 50 | 37 | 0 |
| 2 | n-Hexane | 36 | 64 | 64 | 50 | 31 | 6 | 6 |
| 3 | 4 unmated females | 30 | 97** | 93** | 80 | 53 | 40 | 10 |
| 4 | 8 unmated males | 30 | 100** | 100*** | 100*** | 97*** | 93*** | 93*** |
| 5 | CLSA extract | 27 | 100** | 100*** | 100*** | 89** | 85*** | 48*** |
| 6 | 5 µl of synth. mixture | 30 | 100** | 100*** | 100*** | 100*** | 83** | 46*** |

TABLE 1-continued

Reaction of unmated females of Hylotrupes bajulus to various scent sources

| No. | Scent source | Number of unmated females (n) | Start (%) | Reaching | | | | Searching/ staying in the vicinity of the scent source (%) |
|---|---|---|---|---|---|---|---|---|
| | | | | Zone I (%) | Zone II (%) | Zone III (%) | Zone IV (%) | |
| 7 | 5 μl of synth. mixture | 32 | 100*** | 100*** | 100*** | 97*** | 78*** | 19* |
| 8 | (3R)-3-Hydroxy-hexan-2-one | 32 | 100*** | 100*** | 97*** | 91*** | 73* | 43*** |
| 9 | Mixture of (2S, 3R)- and (2R, 3R)-hexane-2,3-diol | 32 | 97** | 97** | 91** * | 88** | 66* | 56*** |
| 10 | Hexane-2,3-dione | 30 | 87 | 83* | 83 | 63 | 33 | 7 |

Asterisks show significant differences ($\chi^2$ test) to the blank experiment (*[p ≦ 0,05]],  [p ≦ 0,01], * [p ≦ 0,001]).

Example 9
Experiment in the Wind Tunnel with *Pyrrhidium sanguineum*

The animals came from collected oak. The adult beetles were isolated in vials immediately after their appearance from the breeding wood. The experimental animals were employed as soon as 4–7 days after their appearance from the oak branches.

The keeping of the experimental animals, the construction of the wind tunnel and the experimental conditions were kept for the comparison as in the wind tunnel experiment on *Hylotrupes bajulus* (cf. Example 8). An experimental temperature of 22° C. was chosen.

The wind velocity in the wind tunnel tube was restricted by additional gauze layers in front of the wind side of the fan. It was 0.31 m/sec at the starting screen, 0.44 m/sec in the center of the tube (on the border between zones II and III) and 0.94 m/sec at the fan screen. The wind velocities in the peripheral regions were in each case somewhat higher than in the center of the tube cross section.

The results of the experiments are compiled in Table 2.

The experimental combinations 2./3./4./6./8./9./10. from the wind tunnel experiment with *Hylotrupes bajulus* (Example 8) were adopted as stimulants. A difference was that in the 3rd experimental batch the number of unmated females in the gauze container was increased to 8 individuals. For batch 6, a mixture of 8% by weight of (2R,3R)-hexane-2,3-diol (31% ee) and 92% by weight of (2S,3R)-hexane-2,3-diol (34% ee) was used.

The mated females were employed repeatedly in the experiments with batch 1 and batch 4 24 h after mating. As some females at this point in time had already reached their average lifetime, the old and weak females (17–14 individuals) were taken from the experiment.

The assessment of the behavior in the wind tunnel was carried out as in the case of *Hylotrupes bajulus*.

TABLE 2

Reaction of unmated females of Pyrrhidium sanguineum to various scent sources

| No. | Scent source | Number of unmated females (n) | Start (%) | Reaching | | | | Searching/ staying in the vicinity of the scent source (%) |
|---|---|---|---|---|---|---|---|---|
| | | | | Zone I (%) | Zone II (%) | Zone III (%) | Zone IV (%) | |
| 1 | n-Hexane | 30 | 100 | 87 | 73 | 47 | 20 | 0 |
| 2 | 8 unmated females | 12 | 100 | 100 | 83 | 50 | 0 | 0 |
| 3 | 8 unmated males | 30 | 100 | 97 | 93* | 77* | 77*** | 57*** |
| 4 | 5 μl of synth. mixture | 30 | 100 | 100* | 80 | 67 | 63*** | 43*** |
| 5 | (3R)-3-Hydroxy-hexan-2-one | 30 | 100 | 93 | 87 | 77* | 70*** | 30** |
| 6 | Mixture of (2S, 3R)- and (2R, 3R)-2,3-hexane diol | 24 | 100 | 88 | 58 | 46 | 38 | 33*** |
| 7 | 2,3-Hexanedione | 24 | 100 | 88 | 54 | 38 | 17 | 0 |

Asterisks show significant differences ($\chi^2$ test) to the blank experiment (*[p ≦ 0,05]],  [p ≦ 0,01], * [p ≦ 0,001]).

We claim:

1. A mixture comprising one stereoisomer of 3-hydroxyhexan-2-one and two stereoisomers of hexane-2,3-diol.

2. A mixture as claimed in claim 1, wherein said stereoisomer of 3-hydroxyhexan-2-one is (3R)-3-hydroxyhexan-2-one.

3. A mixture as claimed in claim 1, wherein said stereoisomers of hexane-2,3-diol are (2S,3R)-hexane-2,3-diol and (2R,3R)-hexane-2,3-diol.

4. A mixture as claimed in claim 1, which comprises
   a) from 70 to 100 parts by weight of (3R)-3-hydroxyhexan-2-one,
   b) from 0.01 to 7 parts by weight of (2R,3R)-hexane-2,3-diol,
   c) from 0.01 to 20 parts by weight of (2S,3R)-hexane-2,3-diol.

5. The mixture of claim 4, further comprising
   d) from 0.01 to 5 parts by weight of hexane-2,3-dione and/or
   e) from 0.01 to 7 parts by weight of a racemic mixture of 2-hydroxyhexan-3-one.

6. A process for preparing a mixture for controlling *Hylotrupes bajulus* and/or *Pyrrhidium sanguineum* as claimed in claim 1, which comprises preparing its components separately and mixing them with one another in a ratio that is effective to control *Hylotrupes bajulus* and/or *Pyrrhidium sanguineum*.

7. A process for controlling *Hylotrupes bajulus* and/or *Pyrrhidium sanguineum* by means of the mating disruption method, which comprises applying a mixture as claimed in claim 1 in an amount wherein the female organisms of the species are disrupted in finding the male organisms.

8. The mixture of claim 2, wherein (3R)-3-hydroxyhexan-2-one has an enantiomeric excess of from 70–100%.

9. The mixture of claim 3, wherein (2S, 3R)-hexane-2,3-diol has an enantiomeric excess of 20–50%.

10. The mixture of claim 3, wherein (2R, 3R)-hexane-2,3-diol has an enantiomeric excess of 15–45%.

11. The mixture of claim 3, wherein (2S, 3R)-hexane-2,3-diol and (2R, 3R)-hexane-2,3-diol are present in a molar ratio of 3:1 to 4:1.

12. A composition suitable for controlling *Hylotrupes bajulus* and/or *Pyrrhidium sanguineum* by the monitoring, capture or mating disruption method, comprising an effective amount of a mixture as claimed in claim 1 and a liquid or solid carrier.

13. A process for controlling *Hylotrupes bajulus* and/or *Pyrrhidium sanguineum* by means of the monitoring method, which comprises applying a mixture as claimed in claim 1 in a trap in an amount wherein the female organisms of the species are attracted to the trap and trapped therein.

14. A process for controlling *Hylotrupes bajulus* and/or *Pyrrhidium sanguineum* by means of the capture method, which comprises
   applying a mixture as claimed in claim 1 to a lure or trap in an amount wherein the female organisms of the species are attracted to the lure or trap, and
   applying an insecticide to the lure or trap and/or to the area in the immediate vicinity of the lure or trap.

15. A composition suitable for controlling *Hylotrupes bajulus* and/or *Pyrrhidium sanguineum*, consisting essentially of an effective amount of (2S, 3R)-hexane-2,3-diol and (2R, 3R)-hexane-2,3-diol and a liquid or solid carrier.

16. A process for controlling *Hylotrupes bajulus* and/or *Pyrrhidium sanguineum* by means of a monitoring method, comprising:
   applying a composition as claimed in claim 15 to a trap in an amount that the female organisms of the species are attracted to the trap and trapped therein.

17. A process for controlling *Hylotrupes bajulus* and/or *Pyrrhidium sanguineum* by means of a capture method, comprising:
   applying a composition as claimed in claim 15 to a lure or trap in an amount that the female organisms of the species are attracted to the lure or trap, and applying an insecticide to the lure or trap and/or to the area in the immediate vicinity of the lure or trap.

18. A process for controlling *Hylotrupes bajulus* and/or *Pyrrhidium sanguineum* by means of a mating disruption method, comprising:
   applying a composition as claimed in claim 15 in the atmosphere in the area of the plant crop to be protected, in an amount that the female organisms of the species are disrupted from finding the male organisms of the species.

19. A process for controlling *Hylotrupes bajulus* and/or *Pyrrhidium sanguineum* by means of a mating disruption method, which comprises applying a composition as claimed in claim 15 in an amount that the female organisms of the species are disrupted in finding the male organisms.

20. A mixture consisting essentially of (2S, 3R)-hexane-2,3-diol and (2R, 3R)-hexane-2,3-diol.

* * * * *